(12) United States Patent
Yang et al.

(10) Patent No.: US 7,630,148 B1
(45) Date of Patent: Dec. 8, 2009

(54) SYSTEM FOR PROVIDING ZOOM, FOCUS AND APERTURE CONTROL IN A VIDEO INSPECTION DEVICE

(75) Inventors: Dongmin Yang, Syracuse, NY (US); Theodore A. Chilek, Skaneateles, NY (US); Thomas Karpen, Skaneateles, NY (US)

(73) Assignee: GE Inspection Technologies, LP, Lewistown, PA (US)

( * ) Notice: Subject to any disclaimer, the term of this patent is extended or adjusted under 35 U.S.C. 154(b) by 42 days.

(21) Appl. No.: 12/136,839

(22) Filed: Jun. 11, 2008

(51) Int. Cl.
*G02B 9/08* (2006.01)

(52) U.S. Cl. .................. 359/740; 359/676; 359/664; 359/738; 600/109; 600/168

(58) Field of Classification Search ............... 359/676, 359/684, 738, 740; 348/65, 72; 600/109, 600/168
See application file for complete search history.

(56) References Cited

U.S. PATENT DOCUMENTS 4,777,524 A * 10/1988 Nakajima et al. ............. 348/76
6,069,651 A *  5/2000 Tsuyuki et al. ............... 348/75

* cited by examiner

*Primary Examiner*—Joseph Martinez
(74) *Attorney, Agent, or Firm*—GE Global Patent Operation (57) ABSTRACT

An optical system for a remote video inspection device including an elongated probe for inspection of target objects, comprising: an imager located distally within the probe, wherein the imager receives an image of the target object; a focus lens group located within the probe, the focus lens group comprising a variable aperture and at least one focus lens; a zoom lens group located within the probe, the zoom lens group comprising at least one zoom lens, wherein the movement of the zoom lens group in relation to the imager changes the magnification of the image; a tip lens located further from the imager than the focus lens group and the zoom lens group, wherein the distance between the tip lens and the imager is fixed; wherein a first movement of the focus lens group proportional to the movement of the zoom lens group provides an initial image focus, and a second movement of the focus lens group independent of the movement of the zoom lens provides a final image focus and proportional changes to the size of the variable aperture.

20 Claims, 5 Drawing Sheets

SYSTEM FOR PROVIDING ZOOM, FOCUS AND APERTURE CONTROL IN A VIDEO INSPECTION DEVICE

BACKGROUND OF THE INVENTION

This invention relates generally to video inspection and more particularly to a zoomable, focus adjustable and aperture variable optical system for video inspection devices.

Video inspection devices, such as video endoscopes, can be used to inspect target objects to identify and analyze flaws and defects in the objects both during and after an inspection. Often times, inspections are performed in small environments such as inside aircraft engines and small pipes. Typically, these environments are poorly illuminated with the only source of light being the endoscope's own light source (e.g., a fiber optic bundle that transmits light from a proximally located lamp, LED or laser, or a distally located lamp or LED). In order for video inspection devices to be effective in maneuvering in these environments, they must be of small diameter, typically less than 10 mm, and exhibit a small distal rigid length, typically less than 20 mm, in order to navigate through locations containing small bending radii. In addition, video inspection devices require versatility in providing wide fields of view, typically up to 120 degrees or greater, in order to provide a more complete view of a target object, while at the same time providing a large depth of field for maintaining a clear image when the inspection device is placed in close proximity to an object. Detailed inspection of objects often requires the ability to observe them from very close distances, typically less than 5 mm. At close distances the illumination light is typically sufficient to produce a bright, high quality image, but a sufficient depth of field is required for viewing 3D objects. Other times, general device navigation and inspection applications require inspectors to view objects from greater distances. When the inspection device is located further away from a given inspection target maintaining sufficient image brightness may be problematic. As such, video inspection devices require an aperture capable of compensating for variable lighting requirements and depths of field as the device is moved closer to or farther from a given inspection target.

Video inspection systems today are typically comprised of a primary optical system exhibiting a fixed, far focused, small field of view on the order of 40 to 50 degrees. The primary optical system provides a large depth of field, highest contrast and brightest image possible for a given endoscope. This arrangement allows for general navigation and distant general inspection of an object of interest, in addition to limited magnification change achievable by pushing the lens system closer to the inspection target within its depth of field. To provide increased magnification at closer focus distances and/or a wider field of view, typically up to 120 degrees, various optical systems can be installed on the forward end of the inspection probe to alter the optical characteristics of the probe and provide a desired field of view and focus distance. These optical systems are often referred to as tips and can be removable. The drawback of this arrangement is that each tip provides a discrete field of view and focus distance change. In addition, the inspector operating the video inspection device is required to pull the probe back out from the inspection site, change the tip, and reinsert the probe if the inspector wishes to change the level of magnification. This can be a time consuming process, and can result in the inspector's inability to relocate the specific site of interest. Alternatively, there are also manually adjustable tips for which the focus can be set prior to inspection. However, such tips can be difficult for the inspector to use since the inspector must know at what distance to focus the tip before using it, and then subsequently be able to accurately set that focus.

Video inspection devices today generally lack an auto-focus mechanism and contain optical systems that are designed to have a fixed focal length with a large depth of field that is sufficient to produce adequate image quality over the typical range of inspection distances. Having this fixed focal length results in all but a limited range of probe focus distances not having the best focus, image quality, contrast and resolution possible. In addition, in order to achieve a large depth of field, a small aperture size is commonly utilized, decreasing image brightness and achievable image contrast and resolution. Typically, the aperture is of a fixed size and position, designed both to facilitate a desired depth of field given a particular lens system diameter, and to minimize distortion and other optical aberrations associated with a given lens arrangement, resulting in a fixed F Number. This inherently results in conflicting goals of achieving good image quality within an acceptable depth of field at close inspection distances while providing a clear, bright image at farther inspection distances.

The design of a video inspection system able to perform optical zooming, focus adjustment and aperture variation is constrained, in part, because of space limitations associated with narrow diameter inspection probes, and the inability to place an optical system capable of varying its focal length within the limited space of the probe. Some devices attempt to provide optical zoom and focus adjustment capabilities using costly, complex optical arrangements consisting of numerous lenses that are difficult to fit within an endoscope. Although several existing video inspection devices offer a zooming capability, the zoom feature is typically that of a digital zoom, a method limited by the resolution provided by the charged coupled device (CCD) or imager. In digital zoom systems, as the zoom level is increased, the resolution and image quality decreases.

The physical conditions of the typical video inspection environment in which video inspection devices operate require that inspection devices be versatile and rugged. In situations in which the probe is used to inspect small diameter pipes, the ability to view the environment from a side-facing surface of the probe rather than the forward-facing surface would be beneficial. Because of these space limitations, the distal end of the video inspection device must be of a fixed rigid length. In addition, the ability to operate the video inspection device in environments up to 80 degrees Celsius, such as a hot engine or turbine, is sometimes necessary and cost effective, as opposed to first waiting for the engine or turbine to cool down before performing the inspection. In situations in which the video inspection device is exposed to liquid environments, such as water, excellent sealing of the device to prevent the liquid from entering the probe is necessitated. Finally, because the typical video inspection environment can be an industrial setting that subjects the probe to potential dropping or being struck by other objects, video inspection devices should be mechanically strong enough to endure harsh environments and accidental mishandling.

One potential method of providing a focus and zoom capability is the use of a liquid lens. In a liquid lens, the optical properties of the lens are altered by the electrostatic pressure applied to a transparent, non-permeable membrane that separates two liquid materials, typically water and oil, when a voltage is applied across those liquids. However, the liquid lens solution has limited practical applicability in a video inspection device as the technology today requires a large diameter lens fixture, has a narrow working temperature range typically up to 60 degrees Celsius, and requires a high drive voltage. Similarly, other conventional zoom and focus systems employed in cameras outside of the video inspection device field are limited in their application to the video inspection field by their size and inability to operate in the extreme environments encountered in the inspection field. It would be advantageous to provide a video inspection device that provides a zoomable, focus adjustable and aperture variable optical system suitable for use in an endoscopic inspection environment.

BRIEF DESCRIPTION OF THE INVENTION

An optical system for a remote video inspection device including an elongated probe for inspection of target objects, comprising: an imager located distally within the probe, wherein the imager receives an image of the target object; a focus lens group located within the probe, the focus lens group comprising a variable aperture and at least one focus lens; a zoom lens group located within the probe, the zoom lens group comprising at least one zoom lens, wherein the movement of the zoom lens group in relation to the imager changes the magnification of the image; a tip lens located further from the imager than the focus lens group and the zoom lens group, wherein the distance between the tip lens and the imager is fixed; wherein a first movement of the focus lens group proportional to the movement of the zoom lens group provides an initial image focus, and a second movement of the focus lens group independent of the movement of the zoom lens provides a final image focus and proportional changes to the size of the variable aperture.

DETAILED DESCRIPTION OF THE INVENTION

Figure 1:
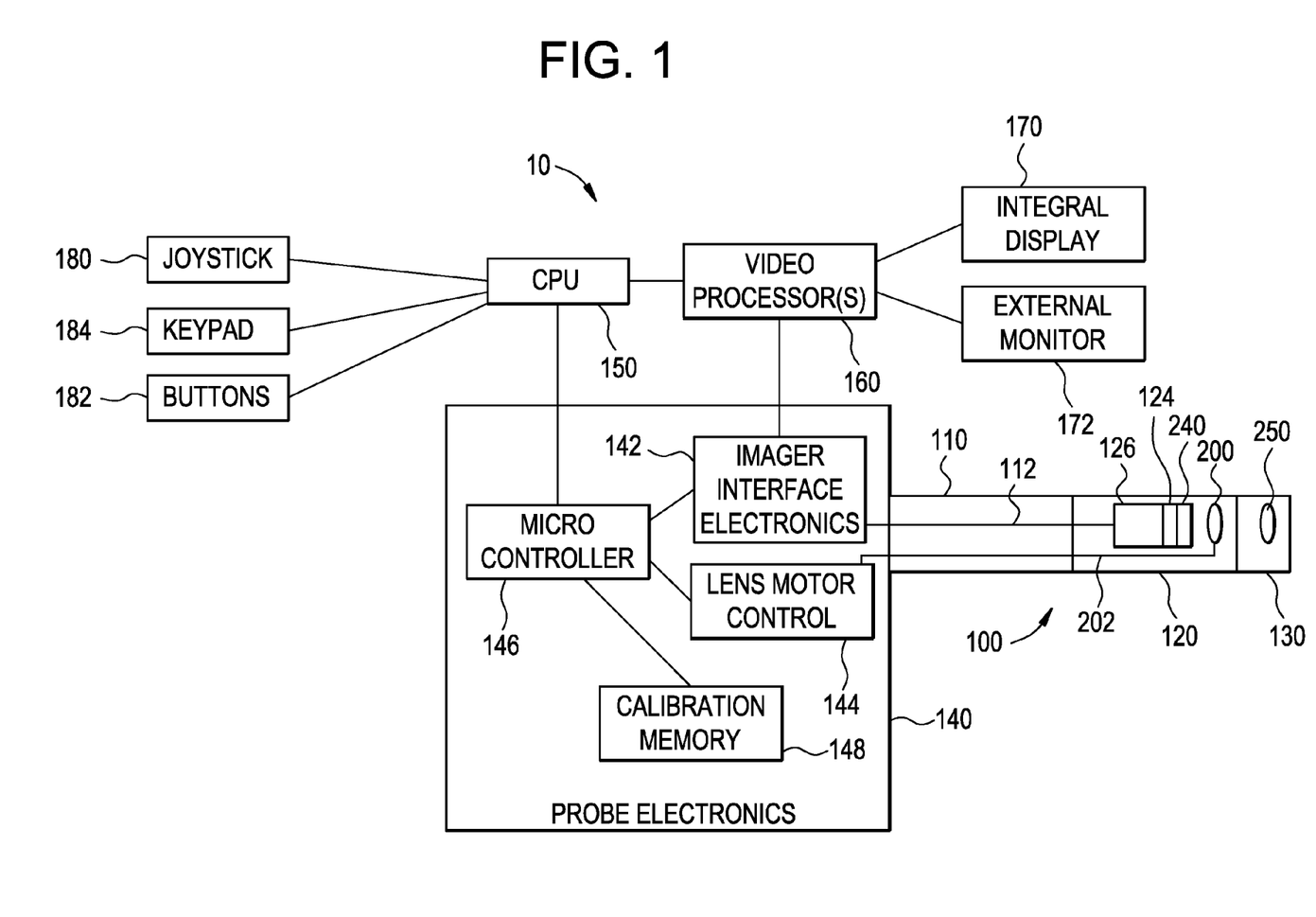
FIG. 1 is a block diagram illustrating one embodiment of a video inspection device.

FIG. 1 illustrates one embodiment of a video inspection device 10. Video inspection device 10 can include an elongated probe 100 comprising an insertion tube 110 and a head assembly 120 disposed at the distal end of the insertion tube 110. Insertion tube 110 can be a flexible, tubular section through which all interconnects between the head assembly 120 and probe electronics 140 are passed. Head assembly 120 can include probe zoom focus optics 200 for guiding and focusing light from the target object onto an imager 124. The imager 124 can be a solid state CCD or CMOS image sensor for obtaining an image of the target object.

A tip 130 can be placed on the distal end of the head assembly 120. The tip 130 can include tip viewing optics 250 (e.g., lenses, windows, or apertures) that work in conjunction with the probe zoom focus optics 200 to guide and focus light from the target object onto an imager 124. The tip 130 can also include illumination LED's (not shown) if the source of light for the video inspection device 10 emanates from the tip 130 or a light passing element (not shown) for passing light from the probe 100 to the target object. The tip 130 can also provide the ability for side viewing by including a waveguide (e.g., a prism) to turn the camera view and light output to the side. The elements that can be included in the tip 130 can also be included in the probe 100. Lenses, waveguides and windows in both the probe 100 and tip 130 can be comprised of molded glass, polished glass or polished sapphire.

The imager 124 can include a plurality of pixels formed in a plurality of rows and columns and can generate image signals in the form of analog voltages representative of light incident on each pixel of the imager 124. The image signals can be propagated through imager hybrid 126, which provides electronics for signal buffering and conditioning, to an imager harness 112, which provides wires for control and video signals between the imager hybrid 126 and the imager interface electronics 142. The imager interface electronics 142 can include power supplies, a timing generator for generating imager clock signals, an analog front end for digitizing the imager video output signal, and a digital signal processor for processing the digitized imager video data into a more useful video format.

The imager interface electronics 142 are part of the probe electronics 140, which provide a collection of functions for operating the video inspection device 10. The probe electronics 140 can also include a calibration memory 148, which stores the calibration data for the probe 100 and/or tip 130. The microcontroller 146 can also be included in the probe electronics 140 for communicating with the imager interface electronics 142 to determine and set gain and exposure settings, storing and reading calibration data from the calibration memory 148, controlling the light delivered to the target object, and communicating with the CPU 150 of the video inspection device 10.

In addition to communicating with the microcontroller 146, the imager interface electronics 142 can also communicate with one or more video processors 160. The video processor 160 can receive a video signal from the imager interface electronics 142 and output signals to various monitors, including an integral display 170 or an external monitor 172. The integral display 170 can be an LCD screen built into the video inspection device 10 for displaying various images or data (e.g., the image of the target object, menus, cursors, measurement results) to an inspector. The external monitor 172 can be a video monitor or computer-type monitor connected to the video inspection device 10 for displaying various images or data.

The video processor 160 can provide/receive commands, status information, streaming video, still video images, and graphical overlays to/from the CPU 150 and may be comprised of FPGAs, DSPs, or other processing elements which provide functions such as image capture, image enhancement, graphical overlay merging, distortion correction, frame averaging, scaling, digital zooming, overlaying, merging, flipping, motion detection, and video format conversion and compression.

The CPU 150 can be used to manage the user interface by receiving input via a joystick 180, buttons 182, and/or keypad 184, in addition to providing a host of other functions, including image, video, and audio storage and recall functions, zoom and focus control, system control, and measurement processing. The joystick 180 can be manipulated by the user to perform such operations as menu selection, cursor movement, slider adjustment, and articulation control of the probe 100, and may include a push-button function. The buttons 182 and/or keypad 184 also can be used for menu selection and providing user commands to the CPU 150 (e.g., freezing or saving a still video image).

Figure 2:
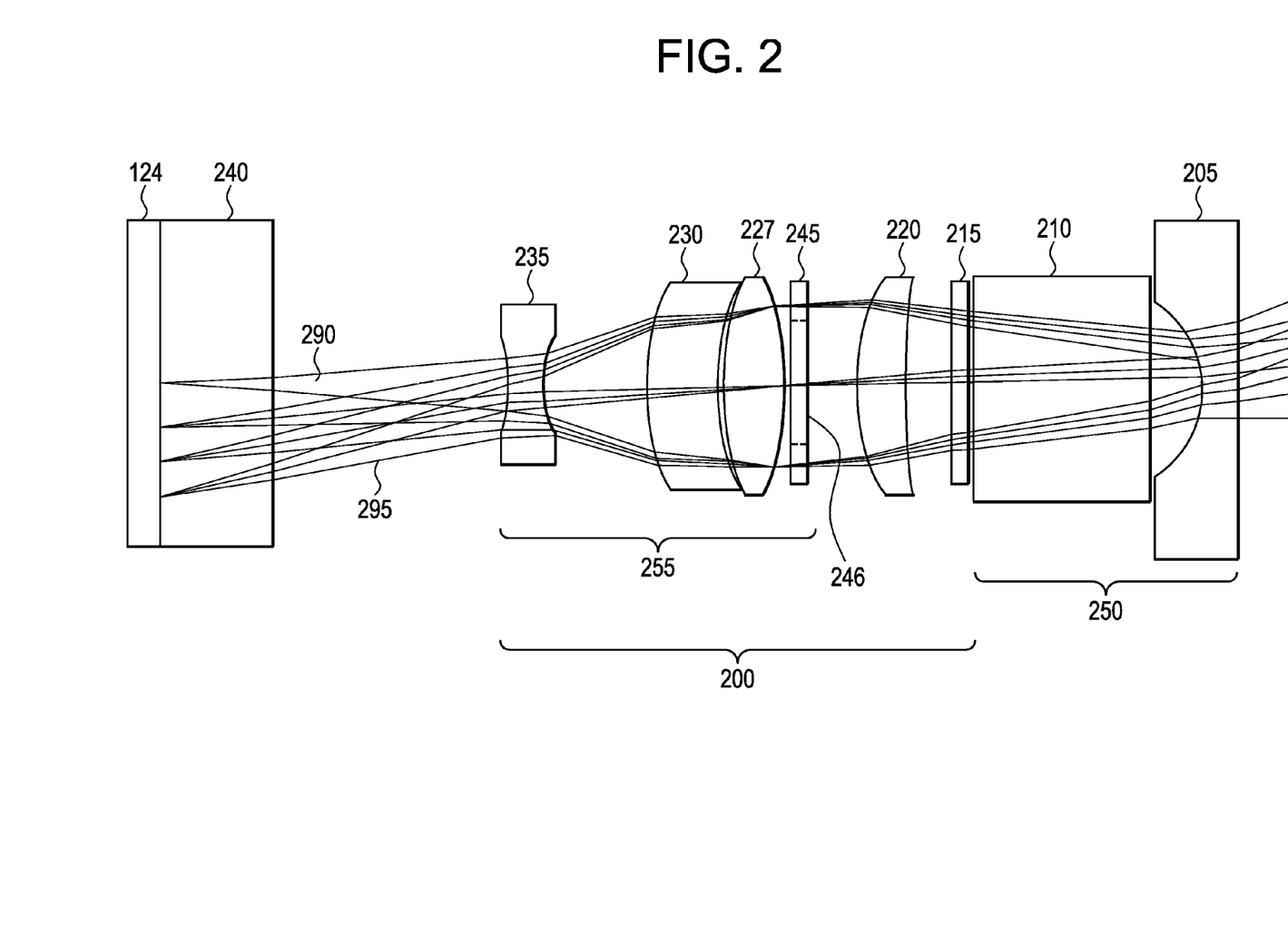
FIG. 2 is a block diagram illustrating one embodiment of a zoomable, focus adjustable and aperture variable optical system using spherical lenses.

FIG. 2 shows, in one embodiment using spherical lenses, a block diagram of the tip viewing optics 250 in combination with the probe zoom focus optics 200, imager window 240 and imager 124. Light pattern 295 can be the path taken by light traveling through the lens system of FIG. 2. Longitudinal axis 290 extends through the centers of tip viewing optics 250, probe zoom focus optics 200, imager window 240 and imager 124. Tip viewing optics 250 can be contained within tip 130 and can consist of a tip lens 205 and waveguide 210. Tip lens 205 can be a polished or molded glass, negative power, plano-concave lens located at the distal end of tip 130, centered on longitudinal axis 290 and aligned such that the primary lens surfaces intersect longitudinal axis 290 at relative right angles. The negative power of the lens expands light entering tip lens 205 through the distal planar surface and can work in conjunction with zoom lens group 220 to provide zoom change. Use of a plano-concave surface acts to provide a larger field of view while maintaining a small diameter lens for use within an endoscope. In addition, the planar distal surface can minimize optical effects when using the probe in a liquid environment, can make sealing the tip 130 easier, and can minimize dirt and particle build-up on the lens surface when conducting inspections in an industrial environment. The distance between the imager 124 and the tip lens 205 remains fixed regardless of the zoom setting of the remote video inspection device 10. In some embodiments, tip lens 205 can be constructed of polished sapphire in order to provide improved scratch resistance. An exemplary prescription for tip lens 205 can be as follows:

| | |
|---|---|
| Distal surface radius | Infinity; clear aperture 3.8 mm |
| Proximal surface radius | 1.37 mm; clear aperture 2.4 mm |
| Glass material | Ohara SBAH28, with refractive index 1.732420; Vd number: 37.9556 |
| Lens center thickness | 0.5 mm |

Waveguide 210 can be located adjacent to the tip lens 205 at its proximal end, centered on longitudinal axis 290 and aligned such that the primary light transmitting surfaces intersect longitudinal axis 290 at relative right angles. Waveguide 210 can be constructed of glass and can act to pass light from the tip lens 205 to the proximal end of tip 130, in addition to maintaining a proper position of tip lens 205 in relation to probe window 215 when tip 130 is attached to head assembly 120. In one embodiment, as shown in FIG. 2, waveguide 210 can be a forward viewing waveguide that transmits light from its distal end to its proximal end. An exemplary prescription for waveguide 210 can be as follows:

| | |
|---|---|
| Distal surface radius | Infinity; clear aperture 2.4 mm |
| Proximal surface radius | Infinity; clear aperture 2.4 mm |
| Glass material | Schott NSF4, with refractive index 1.755131; Vd number: 27.3770 |
| Waveguide center thickness | 2.4 mm |
| Center air gap to tip lens 205 | 0.72 mm |

Figure 3:
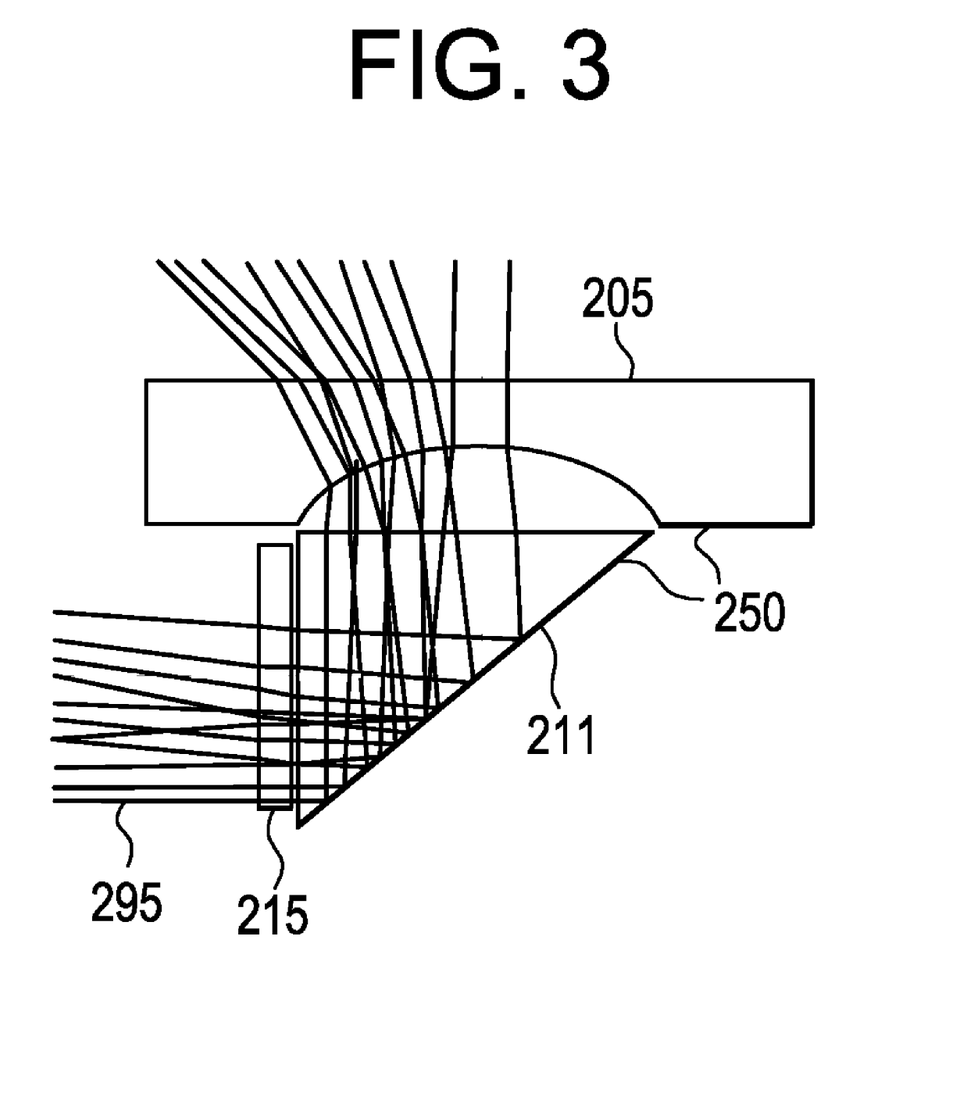
FIG. 3 is a block diagram illustrating one embodiment of a zoomable, focus adjustable and aperture variable optical system using spherical lenses in a side view configuration.

In other embodiments, as shown in FIG. 3, the waveguide 211 can be a right angle prism shaped in order to provide a side viewing capability. In a side viewing embodiment, tip lens 205 can be located on the side of tip 130, passing light through to prism shaped waveguide 211, which redirects the light at an angle, e.g., 90 degrees, towards the proximal end of the tip 130 and into probe window 215.

Tip 130 can be detachably attached or fixedly attached to the distal end of head assembly 120. In embodiments where tip 130 is fixedly attached to the distal end of head assembly 120, both the probe window 215 and waveguide 211 can be made optional.

With reference again to FIG. 2, probe window 215 can be located at the distal end of head assembly 120, centered on longitudinal axis 290 and aligned such that the primary window surfaces intersect longitudinal axis 290 at relative right angles. Probe window 215 can be constructed of planar polished or molded glass or polished sapphire. Polished sapphire can be used to improve the scratch resistance of probe window 215. The planar distal surface can minimize optical effects when using the probe in a liquid environment, can make sealing the head assembly 120 easier, and can minimize the build-up of dirt and particle build-up on the distal surface of probe window 215 when conducting inspections in an industrial environment. An exemplary prescription for probe window 215 can be as follows:

| | |
|---|---|
| Distal surface radius | Infinity; clear aperture 2.3 mm |
| Proximal surface radius | Infinity; clear aperture 2.3 mm |
| Glass material | Sapphire, with refractive index 1.768240; Vd number: 72.2721 |
| Window center thickness | 0.254 mm |
| Center air gap to waveguide 210 | 0.05 mm |

Zoom lens group 220 can be a single molded or polished glass or polished sapphire, positive power, concave-convex lens (e.g., a positive Meniscus lens) located adjacent to the proximal side of the probe window 215 within the head assembly 120, centered on longitudinal axis 290 and aligned such that the primary lens surfaces intersect longitudinal axis 290 at relative right angles. The convex surface of zoom lens group 220 can face proximally towards the variable aperture 245. In other embodiments, zoom lens group 220 can consist of a plurality of lenses. Zoom lens group 220 can be made moveable along the longitudinal axis 290 within the head assembly 120 through the use of a zoom movement mechanism (not shown) (e.g., an electrically driven actuator and associated mechanics). The electrically driven actuator of the zoom movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. Movement can be controlled by an inspector by issuing a zoom-in or zoom-out command through the use of joystick 180, buttons 182 and/or keypad 184. The CPU 150 interprets the zoom command and instructs the micro controller 146 to execute the given zoom command. Micro controller 146, in turn, sends a signal to the lens motor control 144, which sends a signal along wires contained within lens control harness 202 to activate the zoom movement mechanism. As the zoom lens group 220 is moved distally, away from the imager 124, magnification of the image is increased and the field of view is narrowed. Likewise, as the zoom lens group 220 is moved proximally along a longitudinal axis towards the imager 124, the magnification of the image is decreased and the field of view is widened. Light passing through zoom lens group 220 can be directed proximally toward the variable aperture 245. Movement of the zoom lens group 220 can result in a continuous 3× magnification change and a corresponding field of view change from 120 degrees to 40 degrees. An exemplary prescription for zoom lens group 220 can be as follows:

| | |
|---|---|
| Distal surface radius | −20 mm; clear aperture 2.3 mm |
| Proximal surface radius | −3.1 mm; clear aperture 2.4 mm |
| Glass material | Schott NSK16, with refractive index 1.620420; Vd number: 60.3236 |
| Lens center thickness | 0.7 mm |
| Center air gap to probe window | 0.53 mm to 2.31 mm |

Focus lens group 255 can be located within head assembly 120 adjacent to the proximal side of zoom lens group 220, centered on longitudinal axis 290 and aligned such that the primary lens surfaces intersect longitudinal axis 290 at relative right angles. The focus lens group 255 can be comprised of a variable aperture 245, a field flattening lens 235, and a doublet achromatic lens group 225, which can be comprised of a convex-convex lens 227 and a concave-convex lens 230. All of the lenses comprising the focus lens group 255 can be constructed of molded or polished glass or polished sapphire. The achromatic lens group 225 can be located within head assembly 120 adjacent to the proximal side of the variable aperture 245, centered on longitudinal axis 290 and aligned such that the primary lens surfaces intersect longitudinal axis 290 at relative right angles. The achromatic lens group 225 works to correct color and other optical aberrations of the image (e.g., spherical aberrations). The convex-convex lens 227 and concave-convex lens 230 are constructed of different glass or sapphire materials, one of them having a different Abbe number than the other. Together, convex-convex lens 227 and concave-convex lens 230 work to balance the different color dispersion effects created by the different lenses comprising the optical system. Lenses comprised of glass with varying Abbe number combinations can be simulated using an optical simulation program, such as Optical Research Associates'Code V optical design software package, until a combination that provides the required optical aberrations correction is found. The combination of the two lenses, which may or may not have an air space separating them, provides a positive power lens that brings two different wavelengths of light into a common focus. Convex-convex lens 227 can be positioned such that either convex surface can face in either direction, making manufacturing of the achromatic lens 225 easier. Concave-convex lens 230 can be positioned such that the concave surface faces one of the convex surfaces of convex-convex lens 227, while the convex surface faces proximally towards field flattening lens 235. An exemplary of a prescription for convex-convex lens 227 can be as follows:

| | |
|---|---|
| Distal surface radius | 2.70 mm; clear aperture 2.3 mm |
| Proximal surface radius | −2.7 mm; clear aperture 2.3 mm |
| Glass material | Schott NSK5, with refractive index 1.589130; Vd number: 61.2668 |
| Lens center thickness | 1.0 mm |
| Center air gap to aperture 245 | 0.01 mm |

An exemplary of a prescription for concave-convex lens 230 can be as follows:

| | |
|---|---|
| Distal surface radius | −2.25 mm; clear aperture 2.3 mm |
| Proximal surface radius | −3.2 mm; clear aperture 2.3 mm |
| Glass material | Schott NSF5, with refractive index 1.755131; Vd number: 27.3770 |
| Lens center thickness | .84 mm |
| Center air gap to lens 227 | 0.0883 mm |

Light traveling from the variable aperture 245 through the achromatic lens 225 can be directed proximally and incident on the field flattening lens 235, which can be a negative power, concave-concave lens constructed of molded or polished glass or polished sapphire. Field flattening lens 235 can be located proximally to achromatic lens 225 centered on longitudinal axis 290 and aligned such that the primary lens surfaces intersect longitudinal axis 290 at relative right angles. Field flattening lens 235 works to improve the focus of the image incident on the imager 124 by reducing field curvature such that the entirety of the image incident on the imager 124 appears focused. Without field flattening lens 235, the image incident on the imager 124 would only appear focused near the center, with the areas surrounding the center of the image becoming progressively unfocused and distorted the further from the center the image is viewed. Light travels from the proximal side of the achromatic lens 225, passes through the field flattening lens 235, and can be incident on the imager window 240. Field flattening lens 235 can be positioned such that the lesser curved of the concave lens surfaces is facing proximally towards the imager 124. An exemplary prescription for field flattening lens 235 can be as follows:

| | |
|---|---|
| Distal surface radius | −1.8 mm; clear aperture 1.5 mm |
| Proximal surface radius | 4.3 mm; clear aperture 1.8 mm |
| Glass material | Schott NSF10, with refractive index 1.728277; Vd number: 28.5326 |
| Lens center thickness | 0.5 mm |
| Center air gap to lens 230 | 1.3802 mm |

Focus lens group 255 can be made moveable through the use of a focus movement mechanism (not shown) (e.g., an electrically driven actuator and associated mechanics). The electrically driven actuator of the focus movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. When an inspector issues a zoom-in or zoom-out command using joystick 180, buttons 182 and/or keypad 184, micro controller 146 activates the zoom movement mechanism within probe zoom focus optics 200 to move the zoom lens group 220 proximally or distally along the longitudinal axis 290 within the head assembly 120. In conjunction with the movement of zoom lens group 220, focus lens group 255 can be moved proportionally at a different speed in the same longitudinal direction (e.g. through the use of a gear mechanism, electronic speed control, or mechanical cam shaft (not shown)). In one embodiment, the zoom movement mechanism moves both the zoom lens group 220 and the focus lens group 255, thereby providing the ability for the inspector to choose a suitable zoom setting while at the same time maintaining an initial object focus. Having an optical design that allows for proportional movement of both the zoom lens group 220 and focus lens group 255 in the same direction to maintain an initial focus allows for simplification and miniaturization of the optics and movement mechanism, thereby making the system suitable for use in video inspection devices 10. Furthermore, the movement characteristics of the zoom lens group 220 and focus lens group 255 are such that movement of zoom lens group 220 from a one field of view to a narrower field of view occurs through movement in only a single direction, with movement of zoom lens group 220 from one field of view to a wider field of view occurring through movement in the opposite direction.

In order to perform final focusing of the object, the inspector then activates a secondary movement mechanism within the probe zoom focus optics 200 using the joystick 180, buttons 182 and/or keypad 184 that provides fine incremental adjustments in the position of the focus lens group 255 distally or proximally along the longitudinal axis 290 within the head assembly 120. Final focus adjustments to the focus lens group 255 occur independent of zoom lens group 220 motion and can be performed by a focus mechanism (not shown) (e.g., an electrically driven actuator and associated mechanics). The electrically driven actuator of the focus movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. Together, the initial and final focus operations of the focus lens group 220 can provide image focus capability from object distances of 5 mm to infinity. Furthermore, the movement characteristics of the zoom lens group 220 and focus lens group 255 are such that the focus lens group 255 moves in only a single direction as the focus lens group 255 moves from an initial image focus to a final image focus and decreases the distance at which a given target object is in focus. Likewise, the movement of focus lens group 255 is in only a single, opposite direction as the focus lens group 255 moves from an initial image focus to a final image focus and increases the distance at which a given target object is in focus.

The following data shows, in one embodiment, the relative position of the focus lens group 255 in relation to the imager 124 given various zoom lens group 220 positions from imager 124 so as to maintain the correct F/# versus focus distance relationship.

| Field of View (degrees) | Focus Distance (mm) | F/# | Zoom Lens Group Position From Imager (mm) | Focus Lens Position From Imager (mm) | Effective Focal Length (mm) | Magnification |
|---|---|---|---|---|---|---|
| 40 | 2000 | 6 | 10.04 | 8.44 | 4.487 | 0.0022 |
| 40 | 50 | 10 | 10.04 | 8.94 | 4.556 | 0.0952 |
| 40 | 25 | 15 | 10.04 | 9.2 | 4.613 | 0.203 |
| 50 | 2000 | 6 | 9.84 | 7.57 | 3.579 | 0.0018 |
| 50 | 50 | 10 | 9.84 | 7.9 | 3.598 | 0.0736 |
| 50 | 25 | 15 | 9.84 | 8.19 | 3.615 | 0.1517 |
| 60 | 2000 | 60 | 9.62 | 6.99 | 2.981 | 0.0015 |
| 60 | 50 | 10 | 9.62 | 7.22 | 2.985 | 0.0603 |
| 60 | 25 | 15 | 9.62 | 7.41 | 2.988 | 0.1221 |
| 70 | 2000 | 6 | 9.4 | 6.58 | 2.576 | 0.0013 |
| 70 | 50 | 10 | 9.4 | 6.75 | 2.576 | 0.0516 |
| 70 | 25 | 15 | 9.4 | 6.88 | 2.575 | 0.1036 |
| 70 | 15 | 16 | 9.4 | 7.02 | 2.575 | 0.1732 |
| 80 | 2000 | 6 | 9.21 | 6.28 | 2.293 | 0.0011 |
| 80 | 50 | 10 | 9.21 | 6.42 | 2.291 | 0.0457 |
| 80 | 25 | 15 | 9.21 | 6.51 | 2.29 | 0.091 |

-continued

| Field of View (degrees) | Focus Distance (mm) | F/# | Zoom Lens Group Position From Imager (mm) | Focus Lens Position From Imager (mm) | Effective Focal Length (mm) | Magnification |
|---|---|---|---|---|---|---|
| 80 | 15 | 16 | 9.21 | 6.61 | 2.288 | 0.1511 |
| 90 | 2000 | 6 | 9.03 | 6.06 | 2.086 | 0.001 |
| 90 | 50 | 10 | 9.03 | 6.17 | 2.084 | 0.0414 |
| 90 | 25 | 15 | 9.03 | 6.25 | 2.082 | 0.0822 |
| 90 | 15 | 16 | 9.03 | 6.32 | 2.081 | 0.1356 |
| 100 | 2000 | 6 | 8.86 | 5.9 | 1.917 | 0.001 |
| 100 | 50 | 10 | 8.86 | 5.98 | 1.915 | 0.0379 |
| 100 | 25 | 15 | 8.86 | 6.04 | 1.914 | 0.0751 |
| 100 | 15 | 16 | 8.86 | 6.1 | 1.913 | 0.1234 |
| 100 | 10 | 17 | 8.86 | 6.16 | 1.911 | 0.1822 |
| 110 | 2000 | 6 | 8.72 | 5.78 | 1.8 | 0.0009 |
| 110 | 50 | 10 | 8.72 | 5.85 | 1.798 | 0.0355 |
| 110 | 25 | 15 | 8.72 | 5.9 | 1.797 | 0.0702 |
| 110 | 15 | 16 | 8.72 | 5.94 | 1.796 | 0.1151 |
| 110 | 10 | 17 | 8.72 | 5.99 | 1.794 | 0.1693 |
| 120 | 2000 | 6 | 8.26 | 5.47 | 1.492 | 0.0007 |
| 120 | 50 | 10 | 8.26 | 5.48 | 1.491 | 0.293 |
| 120 | 25 | 15 | 8.26 | 5.52 | 1.49 | 0.0576 |
| 120 | 15 | 16 | 8.26 | 5.55 | 1.489 | 0.0939 |
| 120 | 10 | 17 | 8.26 | 5.57 | 1.489 | 0.137 |
| 120 | 5 | 18 | 8.26 | 5.81 | 1.482 | 0.253 |

Variable aperture 245 can be located within focus group 255 adjacent to the distal end of convex-convex lens 227, and can be centered on longitudinal axis 290. Variable aperture 245 moves with focus group 255 and contains an aperture opening 246 centered along the longitudinal axis 290 that extends through the variable aperture 245. The size of the aperture opening 246 can be made larger or smaller depending on the desired amount of light to be passed through the aperture opening 246 and incident on the focus lens group 255. As an inspector adjusts the final focus level of the endoscope, the aperture opening 246 can be proportionally made either smaller, as the focus lens group 255 is moved distally closer to the zoom lens group 220, or larger, as the focus lens group 255 is moved proximally farther from the zoom lens group 220. The aperture opening 246 size can be controlled by the aperture size variation mechanism (not shown) (e.g., an electrically driven actuator and associated mechanics). The electrically driven actuator of the aperture size variation mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. In one embodiment, one movement mechanism controls both the aperture size variation and final focus movement. The following data summarizes, in one embodiment, the aperture sizes for given locations of the focus lens group 255 in relation to the imager 124.

| Field of View (degrees) | Focus Distance (mm) | Aperture Size (mm) | F/# |
|---|---|---|---|
| 40 | 2000 | 2.15 | 6 |
| 40 | 50 | 1.37 | 10 |
| 40 | 25 | 0.99 | 15 |
| 50 | 2000 | 1.77 | 6 |
| 50 | 50 | 1.11 | 10 |
| 50 | 25 | 0.78 | 15 |

-continued

| Field of View (degrees) | Focus Distance (mm) | Aperture Size (mm) | F/# |
|---|---|---|---|
| 60 | 2000 | 1.51 | 60 |
| 60 | 50 | 0.94 | 10 |
| 60 | 25 | 0.65 | 15 |
| 70 | 2000 | 1.33 | 6 |
| 70 | 50 | 0.83 | 10 |
| 70 | 25 | 0.57 | 15 |
| 70 | 15 | 0.56 | 16 |
| 80 | 2000 | 1.21 | 6 |
| 80 | 50 | 0.75 | 10 |
| 80 | 25 | 0.51 | 15 |
| 80 | 15 | 0.5 | 16 |
| 90 | 2000 | 1.12 | 6 |
| 90 | 50 | 0.69 | 10 |
| 90 | 25 | 0.47 | 15 |
| 90 | 15 | 0.46 | 16 |
| 100 | 2000 | 1.04 | 6 |
| 100 | 50 | 0.64 | 10 |
| 100 | 25 | 0.44 | 15 |
| 100 | 15 | 0.42 | 16 |
| 100 | 10 | 0.41 | 17 |
| 110 | 2000 | 0.99 | 6 |
| 110 | 50 | 0.61 | 10 |
| 110 | 25 | 0.42 | 15 |
| 110 | 15 | 0.4 | 16 |
| 110 | 10 | 0.39 | 17 |
| 120 | 2000 | 0.86 | 6 |
| 120 | 50 | 0.53 | 10 |
| 120 | 25 | 0.36 | 15 |
| 120 | 15 | 0.34 | 16 |
| 120 | 10 | 0.33 | 17 |
| 120 | 5 | 0.33 | 18 |

Imager window 240 can be located proximal to the focus lens group 255 and adjacent to the distal side of the imager 124, centered on longitudinal axis 290 and aligned such that the primary window surfaces intersect longitudinal axis 290 at relative right angles. Imager window 240 can be constructed of molded or polished glass or polished sapphire, and can have planar surfaces and constant thickness so as to minimize the optical effects of the window while providing maximum protection to the imager 124. The planar distal surface also acts to reduce dirt and particle collection that can result from the moving parts within the probe or materials left during manufacturing and assembly of the probe. An exemplary prescription for imager window 240 can be as follows:

| | |
|---|---|
| Distal surface radius | Infinity; clear aperture 3.1 mm |
| Proximal surface radius | Infinity; clear aperture 3.6 mm |
| Glass material | Schott NBK7, with refractive index 1.516800; Vd number: 64.1673 |
| Window center thickness | 1.5 mm |
| Center air gap to field flattening lens 235 | 0.15 mm to 4.01 mm |

Figure 4:
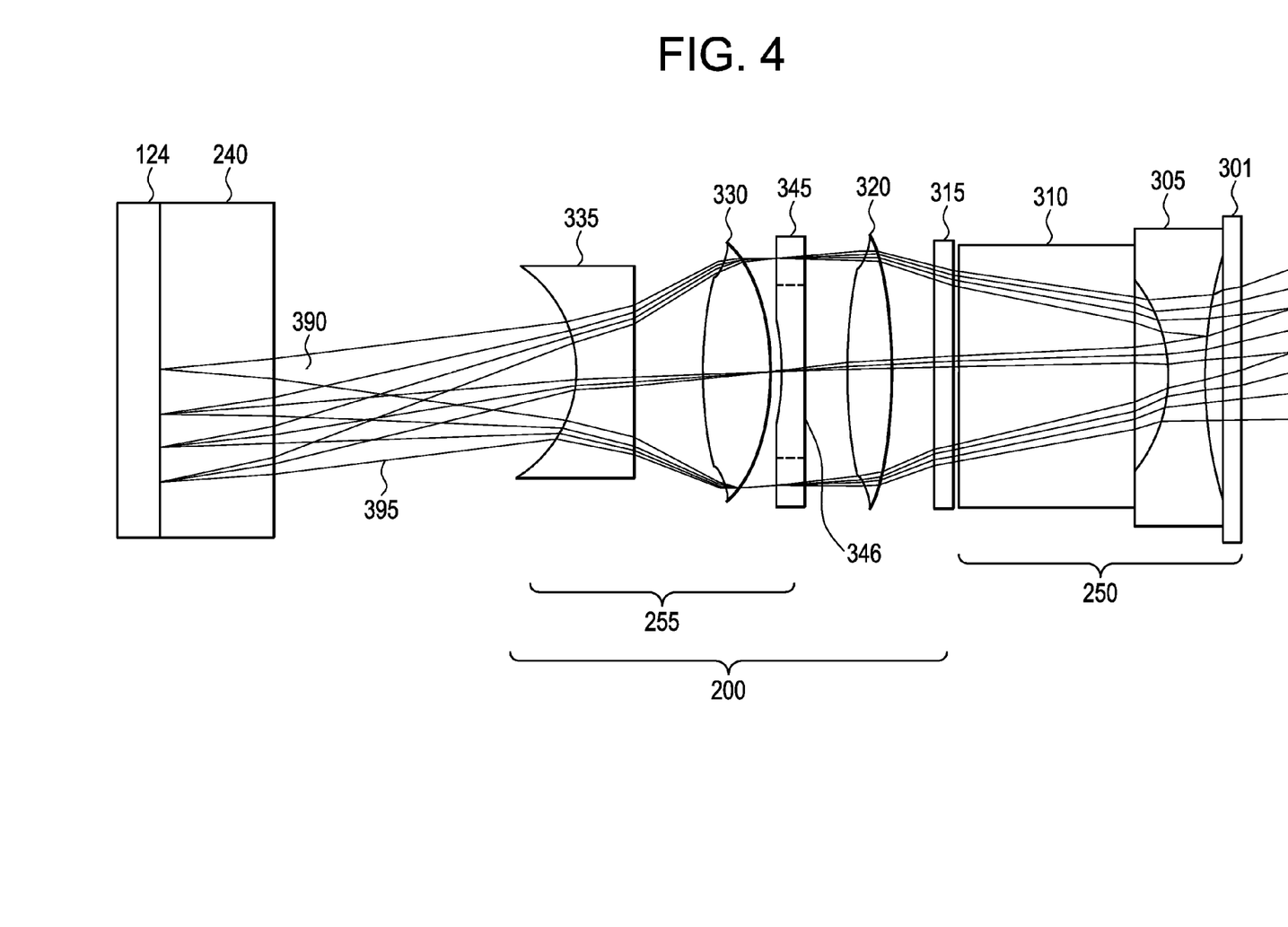
FIG. 4 is a block diagram illustrating one embodiment of a zoomable, focus adjustable and aperture variable optical system using aspherical lenses.

FIG. 4 shows, in another embodiment using aspherical lenses, a block diagram of the tip viewing optics 250 in combination with the probe zoom focus optics 200, imager window 240 and imager 124. Light pattern 395 can be the path taken by light traveling through the lens system of FIG. 4. Longitudinal axis 390 extends through the centers of tip viewing optics 250, probe zoom focus optics 200, imager window 240 and imager 124. Tip viewing optics 250 can be contained within tip 130 and consists of a tip window 301, tip lens 305 and waveguide 310. Tip window 301 can be located adjacent to the distal side of tip lens 305 centered on longitudinal axis 390 and aligned such that the primary window surfaces intersect longitudinal axis 390 at relative right angles. Tip window 301 can be constructed of molded or polished glass or polished sapphire, and can have planar surfaces and constant thickness so as to minimize the optical effects of the window while providing maximum protection to the tip lens 305. The planar distal surface also acts to reduce dirt and particle collection that can result from operation in an industrial environment. In some embodiments, tip window 301 can be constructed of polished sapphire in order to provide improved scratch resistance. In other embodiments, tip window 301 can be made optional. An exemplary prescription for tip window 301 can be as follows:

| | |
|---|---|
| Distal surface radius | Infinity; clear aperture 3.6 mm |
| Proximal surface radius | Infinity; clear aperture 3.6 mm |
| Glass material | Sapphire, with refractive index 1.768240; Vd number: 72.2721 |
| Lens center thickness | 0.254 mm |

Tip lens 305 can be a polished or molded glass, negative power, aspherical concave-spherical concave lens located adjacent to the proximal side of the tip window 301, centered on longitudinal axis 390 and aligned such that the primary lens surfaces intersect longitudinal axis 390 at relative right angles. The negative power expands light entering tip lens 305 through the distal concave surface and can work in conjunction with zoom lens group 320 to provide zoom change. Tip lens 305 can be constructed such that the proximal lens surface is spherical, while the distal surface is aspherical, the aspherical shape working to correct selected optical aberrations created by the lens system. Tip lens 305 can be positioned such that the spherical lens surface faces proximally towards waveguide 310. The distance between the imager 124 and the tip lens 305 remains fixed regardless of the zoom setting of the remote video inspection device 10. An exemplary prescription for tip lens 305 can be as follows:

| | |
|---|---|
| Distal aspherical surface radius | −4.45 mm, $4^{th}$ order coefficient (A) = 0.0124, $6^{th}$ order coefficient (B) = −0.0015; clear aperture 3.3 mm |
| Proximal spherical surface radius | 2.10 mm; clear aperture 2.6 mm |
| Glass material | Schott NLAF2, with refractive index 1.743972; Vd number: 44.8504 |
| Lens center thickness | 0.5 mm |
| Center air gap to tip window 301 | 0.25 mm |

Waveguide 310 can be located adjacent to the tip lens 305 at its proximal end, centered on longitudinal axis 390 and aligned such that the primary light transmitting surfaces intersect longitudinal axis 390 at relative right angles. Waveguide 310 can be constructed of glass and can act to pass light from the tip lens 305 to the proximal end of tip 130, in addition to maintaining a proper position of tip lens 305 in relation to probe window 315 when tip 130 is attached to head assembly 120. In one embodiment, as shown in FIG. 4, waveguide 310 can be a forward viewing waveguide that transmits light with minimal optical effects from its distal end to its proximal end. An exemplary prescription for waveguide 310 can be as follows:

| | |
|---|---|
| Distal surface radius | Infinity; clear aperture 2.5 mm |
| Proximal surface radius | Infinity; clear aperture 2.8 mm |
| Glass material | Schott NSF4, with refractive index 1.755131; Vd number: 27.3770 |
| Waveguide center thickness | 2.4 mm |
| Center air gap to tip lens 305 | 0.4422 mm |

Figure 5:
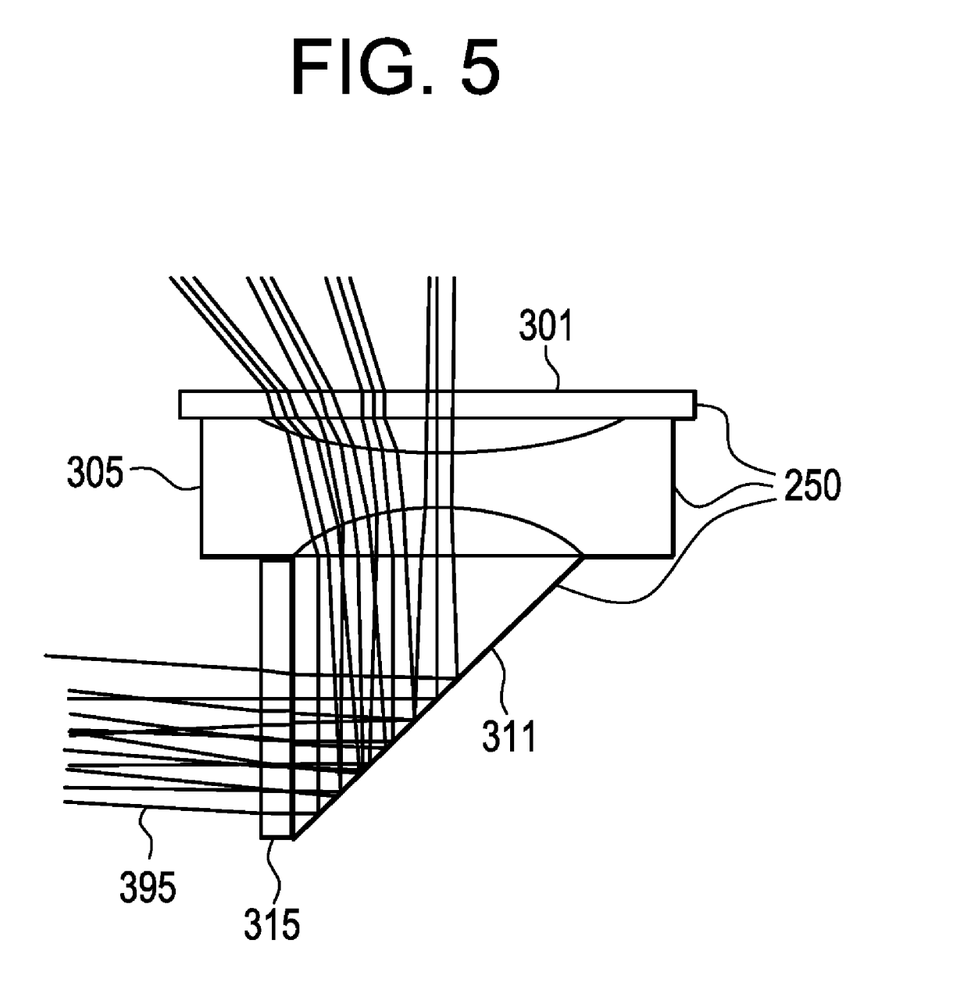
FIG. 5 is a block diagram illustrating one embodiment of a zoomable, focus adjustable and aperture variable optical system using aspherical lenses in a side view configuration.

In other embodiments, as shown in FIG. 5, waveguide 311 can be a right angle prism shaped in order to provide a side viewing capability. In a side viewing embodiment, tip lens 305 can be located on the side of tip 130, passing light through to prism shaped waveguide 311, which redirects the light 90 degrees towards the proximal end of the tip 130 and into probe window 315.

Tip 130 can be detachably attached or fixedly attached to the distal end of head assembly 120. In embodiments where tip 130 is fixedly attached to the distal end of head assembly 120, both the probe window 315 and waveguide 311 can be made optional.

With reference again to FIG. 4, probe window 315 can be located at the distal end of head assembly 120, centered on longitudinal axis 390 and aligned such that the primary window surfaces intersect longitudinal axis 390 at relative right angles. Probe window 315 can be constructed of planar polished or molded glass or polished sapphire. Polished sapphire can be used to improve the scratch resistance of probe window 315. The planar distal surface can minimize optical effects when using the probe in a liquid environment, can make sealing the head assembly 120 easier, and can minimize dirt and particle build-up on the distal surface of probe window 315 when conducting inspections in an industrial environment. An exemplary prescription for probe window 315 can be as follows:

| | |
|---|---|
| Distal surface radius | Infinity; clear aperture 3.0 mm |
| Proximal surface radius | Infinity; clear aperture 3.0 mm |
| Glass material | Sapphire, with refractive index 1.768240; Vd number: 72.2721 |
| Window center thickness | 0254 mm |
| Center air gap to waveguide 310 | 0.05 mm |

Zoom lens group 320 can be a single molded or polished glass or polished sapphire, positive power, spherical convex-aspherical convex lens located within head assembly 120 adjacent to the proximal side of the probe window 315, centered on longitudinal axis 390 and aligned such that the primary lens surfaces intersect longitudinal axis 390 at relative right angles. The aspherical surface of zoom lens group 320 can be positioned proximally facing the variable aperture 345. In other embodiments, zoom lens group 320 can consist of a plurality of lenses. Zoom lens group 320 can be made moveable along the longitudinal axis 390 within the head assembly 120 through the use of a zoom movement mechanism (not shown) (e.g., an electrically driven actuator and associated mechanics). The electrically driven actuator of the zoom movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. Movement can be controlled by an inspector by issuing a zoom-in or zoom-out command through the use of joystick 180, buttons 182 or keypad 184. The CPU 150 interprets the zoom command and instructs the micro controller 146 to execute the given zoom command. Micro controller 146, in turn, sends a signal to the lens motor control 144, which sends a signal along wires within lens control harness 202 to activate a zoom movement mechanism. As the zoom lens group 320 is moved distally, away from the imager 124, magnification of the image is increased and the field of view is narrowed. Likewise, as the zoom lens group 320 is moved proximally along a longitudinal axis towards the imager 124, the magnification of the image is decreased and the field of view is widened. Light passing through zoom lens group 320 can be directed proximally toward the variable aperture 345. Movement of the zoom lens group can result in a continuous 3× magnification change and a corresponding field of view change from 120 degrees to 40 degrees. An exemplary prescription for zoom lens group 320 can be as follows:

| | |
|---|---|
| Distal spherical surface radius | 4.3 mm; clear aperture 3.4 mm |
| Proximal aspherical surface radius | −5.2 mm, $4^{th}$ order coefficient (A) = 0.005, $6^{th}$ order coefficient (B) = −0.0001; clear aperture 3.4 mm |
| Glass material | Schott NFK5, with refractive index 1.48749; Vd number: 70.4058 |
| Lens center thickness | 0.7 mm |
| Center air gap to probe window 315 | 0.50 mm to 2.36 mm |

Focus lens group 355 can be located within head assembly 120 adjacent to the proximal side of zoom lens group 320, centered on longitudinal axis 390 and aligned such that the primary lens surfaces intersect longitudinal axis 390 at relative right angles. Focus lens group 355 can be comprised of a variable aperture 345, a double aspherical, positive power convex-convex lens 330 and a spherical field flattening lens 335. Both of the lenses comprising the focus lens group 355 can be constructed of molded or polished glass or polished sapphire. Convex-convex lens 330 can be located adjacent to the proximal side of the variable aperture 345. Both surfaces of convex-convex lens 330 are aspherical, with the surface having a weaker curvature facing proximally towards field flattening lens 335. An exemplary prescription for convex-convex lens 330 can be as follows:

| | |
|---|---|
| Distal aspherical surface radius | 2.55 mm, $4^{th}$ order coefficient (A) = 0.0002, $6^{th}$ order coefficient (B) = −0.0064; clear aperture 3.3 mm |
| Proximal aspherical surface radius | −3.35 mm, $4^{th}$ order coefficient (A) = 0.0187, $6^{th}$ order coefficient (B) = −0.0035, $8^{th}$ order coefficient (C) = 0.001; clear aperture 3.3 mm |
| Glass material | Schott NFK5, with refractive index 1.48749; Vd number: 70.4058 |
| Lens center thickness | 0.95 mm |
| Center air gap to aperture 345 | 0.01 mm |

Light traveling from the variable aperture 345 through the convex-convex lens 330 can be directed proximally and incident on the field flattening lens 335, which can be a negative power, concave-concave lens constructed of molded or polished glass or polished sapphire. Field flattening lens 335 can be located on the proximal side of convex-convex lens 330, centered on longitudinal axis 390 and aligned such that the primary lens surfaces intersect longitudinal axis 390 at relative right angles. Field flattening lens 335 works to improve the focus of the image incident on the imager 124 by reducing field curvature such that the entirety of the image incident on the image 124 appears focused. Without field flattening lens 335, the image incident on the imager 124 would only appear focused near the center, with the areas surrounding the center of the image becoming progressively unfocused the further from the center the image is viewed. Light travels from the proximal side of the convex-convex lens 330, passes through the field flattening lens 335, and can be incident on the imager window 240. An exemplary prescription for field flattening lens 335 can be as follows:

| | |
|---|---|
| Distal surface radius | −100.0 mm; clear aperture 2.4 mm |
| Proximal surface radius | 1.65 mm; clear aperture 2.2 mm |
| Glass material | Schott NSF4, with refractive index 1.755131; Vd number: 27.3770 |
| Lens center thickness | 0.75 mm |
| Center air gap to convex-convex lens 330 | 0.934 mm |

Focus lens group 355 can be made moveable through the use of a focus movement mechanism (not shown) (e.g., an electrically driven actuator and associated mechanics). The electrically driven actuator of the focus movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. When an inspector issues a zoom-in or zoom-out command using joystick 180, buttons 182 and/or keypad 184, micro controller 146 activates a movement mechanism within probe zoom focus optics 200 to move the zoom lens group 320 proximally or distally along the longitudinal axis 390 within the head assembly 120. In conjunction with movement of zoom lens group 320, focus lens group 355 can be moved proportionally at different speeds in the same longitudinal direction (e.g. through the use of a gear mechanism, electronic speed control, or mechanical cam shaft (not shown)). In one embodiment, the zoom movement mechanism moves both the zoom lens group 320 and the focus lens group 355, thereby providing the ability for the inspector to choose a suitable zoom setting while at the same time maintaining an initial object focus. Having an optical design that allows for proportional movement of both the zoom lens group 320 and focus lens group 355 in the same direction to maintain an initial focus allows for simplification and miniaturization of the optics and movement mechanism, thereby making the system suitable for use in video inspection devices 10. Furthermore, the movement characteristics of the zoom lens group 320 and focus lens group 355 are such that movement of zoom lens group 320 from one field of view to a narrower field of view occurs through movement in only a single direction, with movement of zoom lens group 320 from one field of view to a wider field of view occurring through movement in the opposite direction.

In order to perform final focusing of the object, the inspector then activates a secondary movement mechanism within the probe zoom focus optics 200 using the joystick 180, buttons 182 and/or keypad 184 that provides fine incremental adjustments in the position of the focus lens group 355 distally or proximally along the longitudinal axis 390 within the head assembly 120. Final focus adjustments to the focus lens group 355 occur independent of zoom lens group 320 motion, and can be performed by a separate final focus movement mechanism (not shown) (e.g., an electrically driven actuator and associated mechanics). The electrically driven actuator of the focus movement mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. Together, the initial and final focus operations of the focus lens group 320 can provide image focus capability from object distances of 5 mm to infinity. Furthermore, the movement characteristics of the zoom lens group 320 and focus lens group 355 are such that the focus lens group 355 moves in only a single direction as the focus lens group 355 moves from an initial image focus to a final image focus and decreases the distance at which a given target object is in focus. Likewise, the movement of focus lens group 355 is in only a single, opposite direction as the focus lens group 355 moves from an initial image focus to a final image focus and increases the distance at which a given target object is in focus.

The following data shows, in one embodiment, the relative position of the focus lens group 355 in relation to the imager 124 given various zoom lens group 320 positions from imager 124 so as to maintain the correct F/# versus focus distance relationship.

| Field of View (degrees) | Focus Distance (mm) | F/# | Zoom Lens Group Position From Imager (mm) | Focus Lens Position From Imager (mm) | Effective Focal Length (mm) | Magnification |
|---|---|---|---|---|---|---|
| 40 | 2000 | 4 | 9.86 | 8.25 | 4.394 | 0.0022 |
| 40 | 50 | 8 | 9.86 | 8.59 | 4.416 | 0.0906 |
| 40 | 25 | 10 | 9.86 | 8.99 | 4.443 | 0.1879 |
| 50 | 2000 | 4 | 9.6 | 7.21 | 3.463 | 0.0017 |
| 50 | 50 | 8 | 9.6 | 7.43 | 3.464 | 0.0697 |
| 50 | 25 | 10 | 9.6 | 7.66 | 3.464 | 0.1406 |
| 60 | 2000 | 4 | 9.34 | 6.49 | 2.879 | 0.0014 |
| 60 | 50 | 8 | 9.34 | 6.64 | 2.875 | 0.0573 |
| 60 | 25 | 10 | 9.34 | 6.79 | 2.871 | 0.114 |
| 70 | 2000 | 4 | 9.08 | 5.98 | 2.478 | 0.0012 |
| 70 | 50 | 8 | 9.08 | 6.08 | 2.474 | 0.0489 |
| 70 | 25 | 10 | 9.08 | 6.18 | 2.47 | 0.0967 |
| 70 | 15 | 12 | 9.08 | 6.32 | 2.465 | 0.1588 |
| 80 | 2000 | 4 | 8.84 | 5.61 | 2.1957 | 0.0011 |
| 80 | 50 | 8 | 8.84 | 5.69 | 2.1926 | 0.0432 |
| 80 | 25 | 10 | 8.84 | 5.76 | 2.1893 | 0.085 |
| 80 | 15 | 12 | 8.84 | 5.86 | 2.1854 | 0.1386 |
| 90 | 2000 | 4 | 8.63 | 5.35 | 1.995 | 0.001 |
| 90 | 50 | 8 | 8.63 | 5.41 | 1.992 | 0.0391 |
| 90 | 25 | 10 | 8.63 | 5.47 | 1.99 | 0.0767 |
| 90 | 15 | 12 | 8.63 | 5.54 | 1.987 | 0.1247 |
| 100 | 2000 | 4 | 8.44 | 5.17 | 1.846 | 0.0009 |
| 100 | 50 | 8 | 8.44 | 5.21 | 1.844 | 0.0361 |
| 100 | 25 | 10 | 8.44 | 5.25 | 1.842 | 0.0707 |
| 100 | 15 | 12 | 8.44 | 5.31 | 1.839 | 0.1147 |
| 100 | 10 | 13 | 8.44 | 5.36 | 1.837 | 0.1664 |
| 100 | 5 | 15 | 8.44 | 5.51 | 1.83 | 0.3034 |
| 110 | 2000 | 4 | 8.08 | 4.79 | 1.61 | 0.0008 |
| 110 | 50 | 8 | 8.08 | 4.85 | 1.607 | 0.0314 |
| 110 | 25 | 10 | 8.08 | 4.88 | 1.605 | 0.0612 |
| 110 | 15 | 12 | 8.08 | 4.92 | 1.604 | 0.0989 |
| 110 | 10 | 13 | 8.08 | 4.95 | 1.602 | 0.1428 |
| 110 | 5 | 15 | 8.08 | 5.14 | 1.593 | 0.2563 |
| 120 | 2000 | 4 | 7.99 | 4.72 | 1.561 | 0.0008 |
| 120 | 50 | 8 | 7.99 | 4.8 | 1.557 | 0.0304 |
| 120 | 25 | 10 | 7.99 | 4.83 | 1.555 | 0.0592 |
| 120 | 15 | 12 | 7.99 | 4.86 | 1.554 | 0.0966 |

-continued

| Field of View (degrees) | Focus Distance (mm) | F/# | Zoom Lens Group Position From Imager (mm) | Focus Lens Position From Imager (mm) | Effective Focal Length (mm) | Magnification |
|---|---|---|---|---|---|---|
| 120 | 10 | 13 | 7.99 | 4.89 | 1.553 | 0.1379 |
| 120 | 5 | 15 | 7.99 | 4.91 | 1.552 | 0.248 |

Variable aperture 345 can be located within focus group 355 adjacent to the distal end of convex-convex lens 330, and can be centered on longitudinal axis 390. Variable aperture 345 moves with focus group 355, and can contain an aperture opening 346 centered along the longitudinal axis 390 that extends through the variable aperture 345. The size of the aperture opening 346 can be made larger or smaller depending on the desired amount of light to be passed through the aperture opening 346 and incident on the focus lens group 355. As an inspector adjusts the final focus level of the endoscope, the aperture opening 346 can be proportionally made either smaller, as the focus lens group 355 is moved distally closer to the zoom lens group 320, or larger, as the focus lens group 355 is moved proximally farther from the zoom lens group 320. The aperture opening 346 size can be controlled by the aperture size variation mechanism (not shown) (e.g., an electrically driven actuator and associated mechanics). The electrically driven actuator of the aperture size variation mechanism can be, in one embodiment, a small electric motor or piezo actuator, including, for example, an ultrasonic motor or surface acoustic wave motor. In some embodiments ultrasonic motors can produce ultrasonic motion using piezoelectric motion, while others can produce ultrasonic motion using electro-static motion. In one embodiment, one movement mechanism controls both the aperture size variation and final focus movement. The following data summarizes, in one embodiment, the aperture sizes for given locations of the focus lens group 355 in relation to the imager 124.

| Field of View (degrees) | Focus Distance (mm) | Aperture Size (mm) | F/# |
|---|---|---|---|
| 40 | 2000 | 2.47 | 4 |
| 40 | 50 | 1.28 | 8 |
| 40 | 25 | 1.09 | 10 |
| 50 | 2000 | 2 | 4 |
| 50 | 50 | 1.03 | 8 |
| 50 | 25 | 0.86 | 10 |
| 60 | 2000 | 1.7 | 4 |
| 60 | 50 | 0.87 | 8 |
| 60 | 25 | 0.72 | 10 |
| 70 | 2000 | 1.63 | 4 |
| 70 | 50 | 0.83 | 8 |
| 70 | 25 | 0.68 | 10 |
| 70 | 15 | 0.59 | 12 |
| 80 | 2000 | 1.58 | 4 |
| 80 | 50 | 0.8 | 8 |
| 80 | 25 | 0.66 | 10 |
| 80 | 15 | 0.57 | 12 |
| 90 | 2000 | 1.45 | 4 |
| 90 | 50 | 0.74 | 8 |
| 90 | 25 | 0.6 | 10 |
| 90 | 15 | 0.52 | 12 |
| 100 | 2000 | 1.36 | 4 |
| 100 | 50 | 0.69 | 8 |
| 100 | 25 | 0.56 | 10 |
| 100 | 15 | 0.48 | 12 |
| 100 | 10 | 0.46 | 13 |
| 100 | 5 | 0.43 | 15 |
| 110 | 2000 | 1.22 | 4 |
| 110 | 50 | 0.62 | 8 |
| 110 | 25 | 0.5 | 10 |
| 110 | 15 | 0.43 | 12 |
| 110 | 10 | 0.41 | 13 |
| 110 | 5 | 0.37 | 15 |
| 120 | 2000 | 1.19 | 4 |
| 120 | 50 | 0.6 | 8 |
| 120 | 25 | 0.49 | 10 |
| 120 | 15 | 0.42 | 12 |
| 120 | 10 | 0.39 | 13 |
| 120 | 5 | 0.36 | 15 |

In addition to providing continuous zoom, focus and aperture change, the optical system embodiments described herein can exhibit maximum fixed lengths of 14.6 mm and maximum lens diameters of 3.8 mm. As such, the optical systems described herein can all be integrated into probes with fixed rigid length requirements and diameters as small as 6 mm, while allowing space for other functional components (e.g., fiber bundles, working channels, etc.). In addition, the optical systems described herein can provide the same image brightness for any zoom setting at a fixed focus distance as the optical systems can be designed to have the same F number for any zoom setting at a fixed focus distance.

Although the exemplary embodiments described herein all place the focus lens group between the zoom lens group and imager, it is understood that one of skill within the art would be able to design alternative embodiments in which the design and configuration of the various components of the optical system could be rearranged while producing the same optical effect.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An optical system for a remote video inspection device including an elongated probe for inspection of target objects, comprising:
    an imager located distally within said probe, wherein said imager receives an image of said target object;
    a focus lens group located within said probe, said focus lens group comprising a variable aperture and at least one focus lens;
    a zoom lens group located within said probe, said zoom lens group comprising at least one zoom lens, wherein the movement of said zoom lens group in relation to said imager changes the magnification of said image;
    a tip lens located further from said imager than said focus lens group and said zoom lens group, wherein the distance between said tip lens and said imager is fixed;
    wherein said movement of said zoom lens group causes a first movement of said focus lens group proportional to said movement of said zoom lens group providing an initial image focus, and a second movement of said focus lens group independent of said movement of said zoom lens provides a final image focus and proportional changes to the size of said variable aperture.

2. The optical system of claim 1, wherein the size of said variable aperture increases when said second movement of said focus lens group is in a direction that increases the distance at which said target object is in focus.

3. The optical system of claim 1, wherein the size of said variable aperture decreases when said second movement of said focus lens group is in a direction that decreases the distance at which said target object is in focus.

4. The optical system of claim 1, wherein said focus lens group moves in only a single direction as said focus lens group moves from said initial image focus to said final image focus and increases the distance at which said target object is in focus.

5. The optical system of claim 1, wherein said focus lens group moves in only a single direction as said focus lens group moves from said initial image focus to said final image focus and decreases the distance at which said target object is in focus.

6. The optical system of claim 1, wherein said zoom lens group and said focus lens group move in only a single direction as said optical system moves from a first field of view to a narrower second field of view.

7. The optical system of claim 1, wherein said zoom lens group and said focus lens group move in only a single direction as said optical system moves from a first field of view to a wider second field of view.

8. The optical system of claim 1, wherein said zoom lens group is located between said focus lens group and said tip lens, and said variable aperture is located between said focus lens group and said zoom lens group.

9. The optical system of claim 1, further comprising a zoom lens group movement mechanism, wherein said zoom lens group movement mechanism causes said movement of said zoom lens group and said first movement of said focus lens group.

10. The optical system of claim 9, wherein said zoom lens group movement mechanism comprises at least one electrical actuator.

11. The optical system of claim 1, further comprising a focus lens group movement mechanism, wherein said focus lens group movement mechanism causes said second movement of said focus lens group and said proportional changes to said variable aperture.

12. The optical system of claim 11, wherein said focus lens group movement mechanism comprises at least one electrical actuator.

13. The optical system of claim 1, wherein said focus lens group consists of a first focus lens, a second focus lens, and said variable aperture.

14. The optical system of claim 1, wherein said focus lens group consists of a first focus lens, a second focus lens, a third focus lens, and said variable aperture.

15. The optical system of claim 1, wherein said zoom lens group consists of a single zoom lens.

16. The optical system of claim 1 further comprising a waveguide located between said tip lens and said imager.

17. The optical system of claim 16, wherein said waveguide comprises a prism.

18. The optical system of claim 1, wherein said tip lens is located in a detachable tip.

19. The optical system of claim 1, wherein said first movement of said focus lens group is in the same direction as said movement of said zoom lens group.

20. An optical system for a remote video inspection device including an elongated probe for inspection of target objects, comprising:
  an imager located distally within said probe, wherein said imager receives an image of said target object;
  a focus lens group located distally to said imager within said probe, said focus lens group comprising a variable aperture and at least one focus lens, wherein said at least one focus lens is located between said imager and said variable aperture;
  a zoom lens group located distally to said focus lens group within said probe, said zoom lens group comprising at least one zoom lens, wherein the movement of said zoom lens group in relation to said imager changes the magnification of said image;
  a tip lens located in a detachable tip further from said imager than said focus lens group and said zoom lens group, wherein the distance between said tip lens and said imager is fixed;
  wherein said movement of said zoom lens group causes a first movement of said focus lens group and proportional to said movement of said zoom lens group providing an initial image focus, and a second movement of said focus lens group independent of said movement of said zoom lens provides a final image focus and proportional changes to the size of said variable aperture.

* * * * *